United States Patent [19]

Allan

[11] Patent Number: 5,672,828
[45] Date of Patent: Sep. 30, 1997

[54] STRENGTH DETERMINATION OF SHEET MATERIALS BY UTRASONIC TESTING

[75] Inventor: Russell J. Allan, Alphington, Australia

[73] Assignee: Amcor Limited, Victoria, Australia

[21] Appl. No.: 586,765

[22] PCT Filed: Oct. 3, 1994

[86] PCT No.: PCT/AU94/00596

§ 371 Date: Jan. 30, 1996

§ 102(e) Date: Jan. 30, 1996

[87] PCT Pub. No.: WO95/11453

PCT Pub. Date: Apr. 27, 1995

[30] Foreign Application Priority Data

Oct. 22, 1993 [AU] Australia .................... PM-1972

[51] Int. Cl.$^6$ ............................................. G01N 29/18
[52] U.S. Cl. .................................. 73/579; 73/159
[58] Field of Search ....................... 73/159, 597, 599, 73/641, 645, 646, 647, 648, 659

[56] References Cited

U.S. PATENT DOCUMENTS

| | | | |
|---|---|---|---|
| 4,122,724 | 10/1978 | Geithman et al. ............... | 73/588 |
| 4,291,577 | 9/1981 | Baum et al. ..................... | 73/597 |
| 4,688,423 | 8/1987 | Orkosalo ........................ | 73/159 |
| 4,735,087 | 4/1988 | Hourani et al. ................. | 73/597 |
| 4,976,150 | 12/1990 | Deka ............................ | 73/644 |
| 5,398,538 | 3/1995 | Williams et al. ................ | 73/159 |

OTHER PUBLICATIONS

Derwent Abstract Accession No. 84-068158/11, Class S03, SU,A, 1019319 (Mosc Eng Phys Inst) 23 May 1983.

Patent Abstracts of Japan, P-154, p. 144, JP,A, 57-128844 (Mitsubishi Denki K.K.) 10 Aug. 1982.

*Primary Examiner*—Hezron E. Williams
*Assistant Examiner*—Rose M. Miller
*Attorney, Agent, or Firm*—Bell, Seltzer, Park & Gibson, P.A.

[57] ABSTRACT

A method of determining strength and related mechanical properties of paper and similar products, both on-line and off-line using a continuous ultrasonic swept frequency wave transmission and reception system. The invention also provides an apparatus for measuring the strength and related mechanical properties of paper.

13 Claims, 3 Drawing Sheets

STRENGTH DETERMINATION OF SHEET MATERIALS BY UTRASONIC TESTING

The invention relates to a method of determining strength and related mechanical properties of paper and similar products, both on-line and off-line, using an ultrasonic wave transmission and reception system. The invention also provides an apparatus for measuring the strength and related mechanical properties of paper and similar products.

It is generally desirable for manufacturers of paper and like products to measure the mechanical properties of their products to ensure that the product will meet the requirements of their intended uses. Until recently, in order to test these properties, it has been necessary to measure the desired properties from samples, cut from the paper sheet, in the laboratory. This method is particularly time consuming and the results obtained are in no way representative of the properties of the entire sheet or roll.

To overcome the problems associated with the off-line process, Baum and Habeger discuss in U.S. Pat. No. 4,291,572 the development of an on-line method and apparatus for measuring strength properties in paper and in particular an estimation of Young's modulus. Baum and Habeger disclose the use of applying a single ultrasonic pulse or a short burst of pulses of ultrasonic waves to the sheet product and measuring the "time of flight" for the pulse to reach the receiver. Knowing the distance between the transmitter and the receiver, the velocity of the wave can be calculated. Young's modulus can then be estimated from the velocity of the wave. However, there are a number of problems associated with the Habeger and Baum on-line method of measuring Young's modulus and other strength characteristics. In particular, because of the noise associated with an on-line system, it is difficult to segregate the extraneous noise from the transmitted pulsed signal and as such it is quite difficult to accurately identify the pulsed signal and thus calculate the "time of flight" of the pulsed signal. Apart from the problem of noise, there is additionally an interface problem where a mismatch of impedances between the material of the transmitter/receiver and of the product may cause problems with taking measurements. As is often the case, the impedance to the wave of the transmitter/receiver when compared to the impedance to the wave of the sheet product is quite different, resulting in losses of the actual energy transmitted to the sheet product. This results in a change of phase and distortion of the single pulse signal which once again makes it difficult to identify the transmitted signal and to calculate the "time of flight".

Another problem associated with the Habeger and Baum system, and hence the ability to accurately measure the "time of flight" of the pulsed signal, is the presence of reflections of the pulsed signal at the interfaces, (such as air/paper) and sample edges. Reflections as well as noise affect the ability to measure accurately the "time of flight" of a pulsed signal, since similarly the original pulsed signal is difficult to identify from the reflected signals.

Habeger and Baum have taken some steps to address the problems of their system and in particular in relation to the problems of noise, impedance mismatch, and reflections. Extra readings and manipulation of the data or in the case of reflections, waiting until the reflections have subsided, are steps which have been taken in an attempt to miniraise the problems associated with the Habeger and Baum system. However, all of these solutions require a significant amount of time which is not generally available in an on-line procedure. For example, it has been observed that it can take up to six minutes to provide an averaged measured result because of the noise and the measurement technique previously utilised. On a modern paper machine, six minutes on-line represents many kilometers and/or tonnes of paper resulting in significant wastage of product if the sheet product does not meet the strength requirements of the desired purpose.

Another type of instrument has been developed in an attempt to continuously monitor the mechanical properties of paper. The instrument originally designed to monitor the elastic moduli of continuously moving polymeric sheets was adapted to measure elastic modulus on moving wet paper. The apparatus when operated transmits a continuous sonic wave of known constant frequency into the sample, the phase shift that occurs between the transmitter and receiver is measured and the wavelength is determined from the measured phase shift. This approach is termed the "continuous-wave-phase-shift" measurement technique. As was the case with the "pulsed technique" of Habeger and Baum, the "continuous-wave-phase-shift" method has a problem with reflections generated within the sheet product, thus making the identification of the phase of the initially-sent wave extremely difficult. Similarly, in order to ensure that the reading taken is an accurate measurement, a low constant frequency signal is used, however, sonic signals used by the prior art have been found to be generally susceptible to noise, generally external machine (or uncorrelated) noise, which once again makes identification of the propagated wave extremely difficult, leading to inaccurate measurements being obtained.

Thus, it is the object of the present invention to provide a method and apparatus which will overcome some of the problems of the prior art and in particular, measure relatively accurately and preferably on-line, the strength and related properties of materials and in particular, paper sheet product.

The present invention is directed to a method of measuring strength characteristics and related properties in a sheet product including the steps of:

(a) providing a continuous sonic swept frequency wave within the sheet product;

(b) receiving the continuous sonic swept frequency wave; and (c) taking measurements in order to ascertain the time the wave takes to reach the receiver after transmission.

Because of the nature of the signal and in particular, the relationship of frequency and time of the signal, it is possible to utilise a means for filtering desired frequencies from undesirable frequencies such as noise and reflections. In prior art methods such filtering was not possible.

Advantageously, by using a continuous sonic swept frequency wave, it is possible to relatively quickly, quantitatively and accurately measure the "time of flight" of the signal from transmission to reception, and hence relatively accurately measure the strength moduli in the longitudinal, shear and Z-directions. This was not possible with the prior art methods of Baum and Habeger and the "continuous phase shift" method which relied upon the comparison of the pulse shape of the received signal with the transmitted signal, wherein the received signal was often difficult to distinguish from noise and reflections.

Preferably, the swept frequency is an ultrasonic frequency.

Most preferably, in order to ascertain the time the wave takes to reach the receiver after transmission, and hence the necessary strength properties, the change in the frequency of the signal transmitted to that received is determined.

Preferably, the continuous ultrasonic swept frequency wave is a linear sweep with constant amplitude. A linear sweep is where, for a constant sweep rate, the instantaneous frequency varies linearly with time.

Thus, because the instantaneous frequency varies linearly with time from measuring the change in frequency and knowing the distance between the transmitter and receiver, the wave velocity can be calculated.

More preferably, the duration of the linear sweep is equal to the measurement time.

As well as transmission and reception means, the method preferably utilises a means for filtering or separating and comparing desired frequencies from both correlated noise (caused by the excitation signal, such as distortion and reverberation) and uncorrelated noise (which is independent of the excitation signal, for example, the movement of the sheet product and machine noise) as well as reflections. A preferred means for filtering or separating and comparing desired frequencies is a phase locked loop. Other suitable frequency based filters and tracking means may also be advantageously used, including a crystal filter.

The invention also provides an apparatus for measuring strength characteristics and related properties in a sheet including:

(a) means to transmit a continuous ultrasonic swept frequency wave within the sheet product;

(b) means to receive the continuous ultrasonic swept frequency wave; and (c) means for taking measurements in order to ascertain the time the wave takes to reach the receiver after transmission;

Preferably, the means for taking measurements includes a means for filtering, separating and comparing the desired signals and more preferably the frequencies of the signals. Preferably, the means for filtering and comparing the desired signals includes a phase locked loop.

Preferably, the apparatus will include at least one transmission means and preferably one or more reception means. In some embodiments however, such as Z-direction measurement, the transmitter may act as the receiver also.

If more than one reception means is utilised they may be arranged in an array around the transmitter preferably in a circular pattern.

Advantageously, the same transmission/reception arrangements can be used to measure longitudinal, shear and Z-direction moduli, whereas in prior art arrangements, this was not possible and different set-ups were required for each measurement.

Furthermore, due to the use of the continuous swept frequency wave, it is possible to set up sets of transmission/reception systems across the width of the sheet product, wherein respective transmitted frequencies selectively operating within a predetermined range of frequencies and thus each of the systems will not interfere with each other. Thus, unlike in prior art methods where it was extremely difficult, if not impossible to obtain on-line values of strength across the entire width of the material simultaneously, advantageously, the present invention provides a relatively quick and accurate means to obtain this valuable information.

An embodiment of the invention will now be described with reference to the accompanying drawings.

Figure 1:
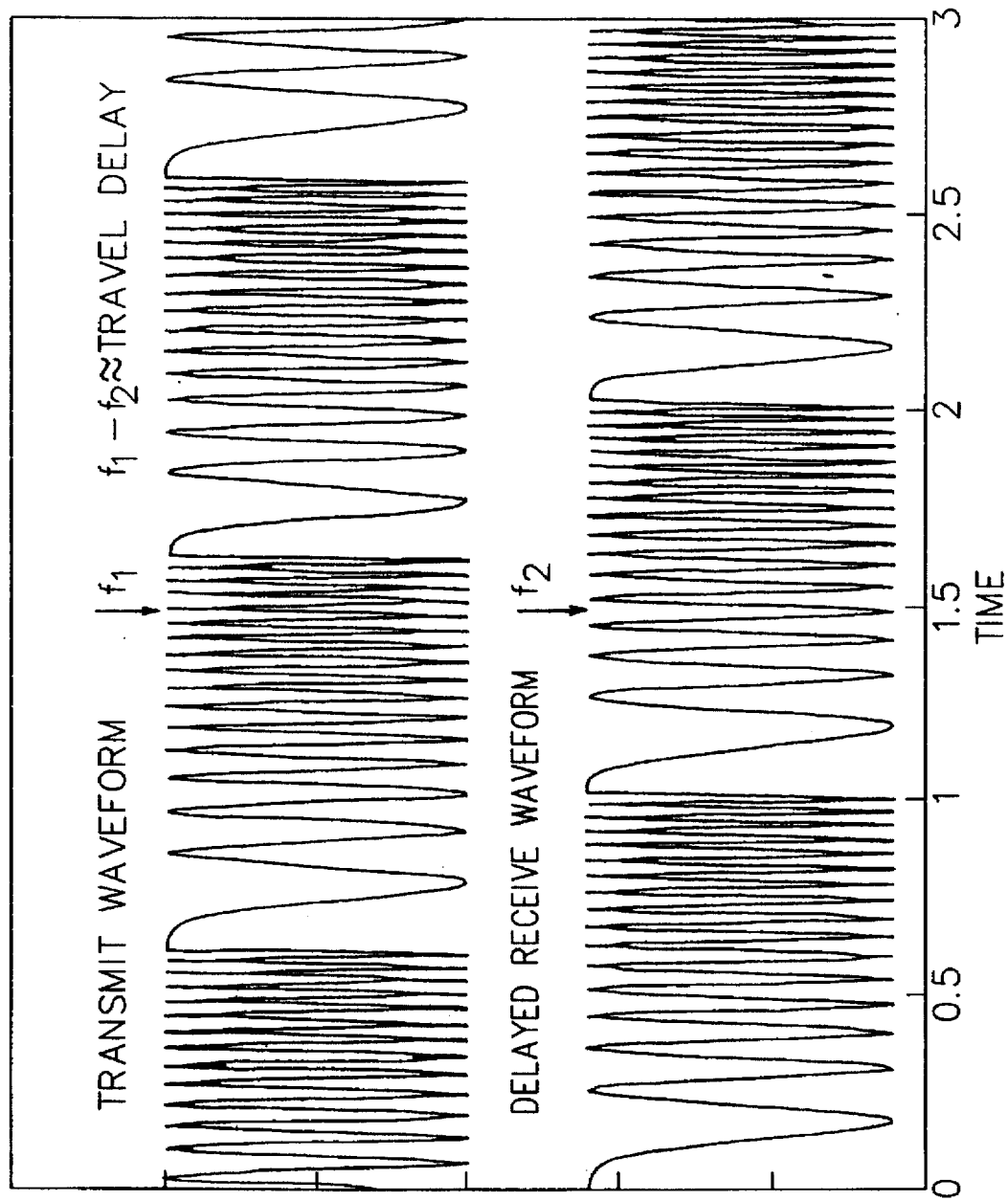
FIG. 1 illustrates a preferred embodiment of the generated and received wave form.

The generated linear waveform or signal is preferably a continuous swept frequency wave. This type of continuous wave has an instantaneous frequency which varies linearly with time, and thus the difference in the instantaneous frequency between the transmitted and received wave is a measure of the delay between transmission and reception. Reference is made to FIG. 1 which illustrates a preferred embodiment of the generated and received wave form.

Figure 2:
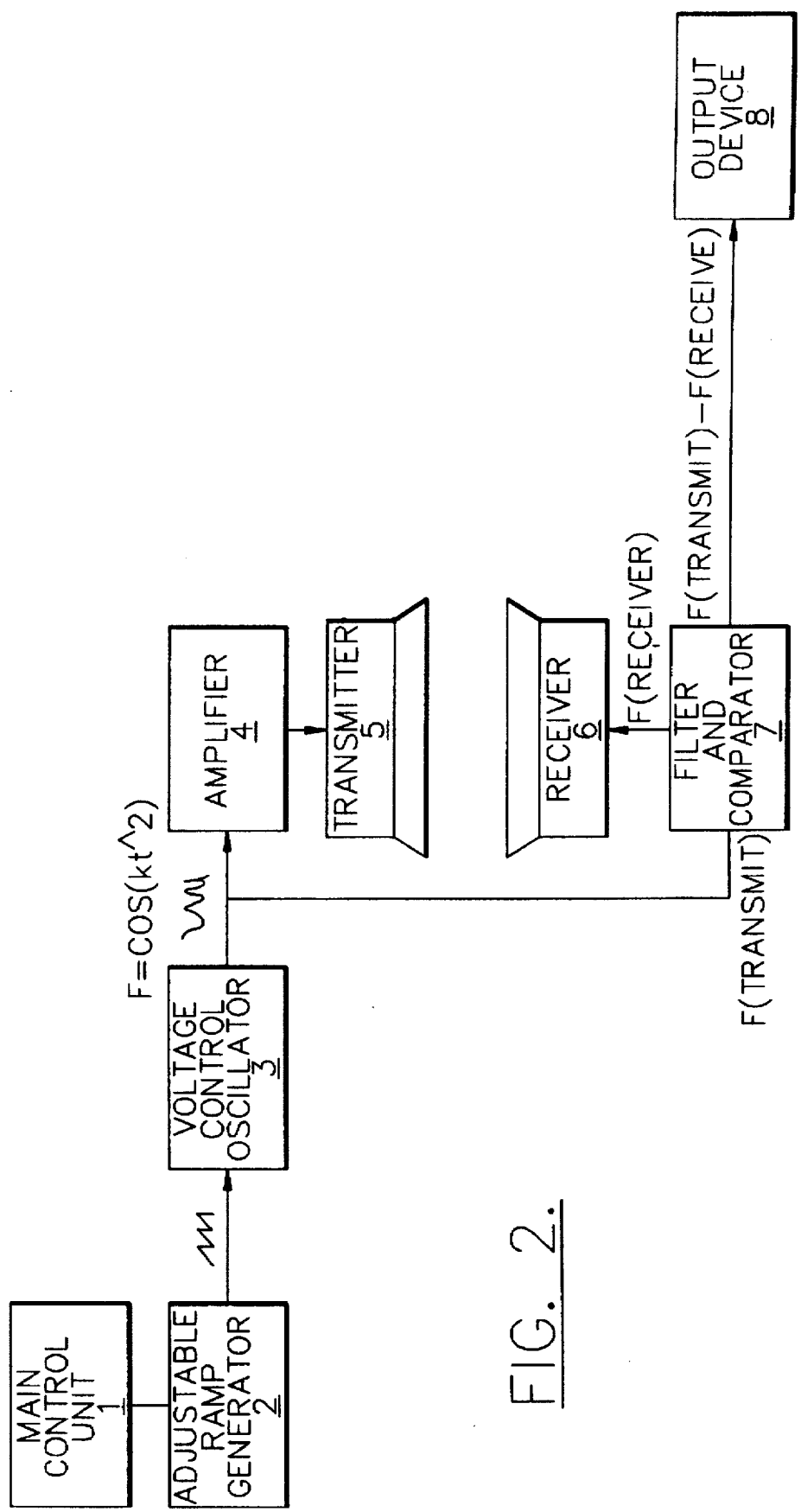
FIG. 2 illustrates a block diagram of the basic preferred components of the apparatus of the present invention.

FIG. 2 illustrates the general outline of the basic components of the apparatus of the present invention. The apparatus generally comprises a means to generate a signal, 1, 2, 3 and 4, a means to transmit a signal, 5, a means to receive the signal, 6, a means to separate or selectively filter and compare the signal received, 7, and an output device, 8.

The waveform is preferably generated using a main control unit (MCU), 1, which controls an adjustable ramp generator, 2, to produce a ramp waveform which is then fed to the voltage controlled oscillator (VCO), 3. The output of the VCO, 3, is the swept frequency wave, which is then, preferably, amplified (item 4) prior to being transmitted. The means to transmit the waveform, 5, in the sheet product are usually piezo-electric devices. Similarly, the means for receiving the wave form, 6, are also piezo-electric devices. In some instances, such as Z-direction measurement, the transmitter can also function as the receiver.

At least one transmitter is used to send the wave signal and preferably one or more receiver devices can be used. The receiver devices may be placed appropriately around, preferably in a circular pattern around, the transmitter device. Similarly, sets of transmitter/receiver systems can be placed along the width of the sheet product, so as to obtain strength readings across the width of the material.

The means to selectively filter and compare the signal received, 7, preferably, selects the desired signal based upon frequency. As indicated previously, the means to selectively filter and compare the signal, 7, preferably collects and filters the received signal and then compares the received signal with the transmitted signal. Preferably the means for selectively filtering and comparing the signal, 7, contains a phase locked loop but similarly a crystal filter may be used. Additionally, the means for separating and comparing the received signal may contain a high gain amplifier (not shown) and a comparator wave "hardener" (not shown).

The high gain amplifier (not shown) increases the low level signal received and any ambient noise. The comparator wave "hardener" preferably follows the high gain amplifier, and as the name suggests "hardens" the signal; converting the signal into a square wave configuration.

The preferred phase locked loop (not shown) for the means for selectively filtering and comparing the signal 7, is a control system which generates an output which is synchronised in frequency and phase to an input signal. Thus, the phase locked loop (not shown) is linked to the wave generator and more preferably the voltage controlled oscillator, 3, wherein the output of the voltage controlled oscillator, 3, is synchronised with the pull range of the phase locked loop (not shown). The "pull range" is the range of frequencies upon which the phase locked loop (not shown) can acquire lock with an incoming signal. In this case, the incoming signal to the phase locked loop (not shown) will be the received signal.

Preferably, the phase locked loop (not shown) will consist of a phase detector and a low pass filter in the forward signal path (from the receiver, 6) and a voltage controlled oscillator (VCO) in the feedback path (to the transmitter, 5). Each of the transmitter/receiver arrangements will preferably utilise a phase locked loop device (PLL) and most preferably a digital PLL. The advantage of using a digital phase locked loop is that the reference input (that the PLL compares the input frequency with) is digital (and thus has minimal drift) and is derived from the transmit signal. This means there is a relatively constant relationship between the PLL reference and the amplified input signal. This relationship is seen as a frequency difference and therefore a stable measure of the experienced delay time.

Additionally, a simple filter (not shown) may be required after the phase locked loop so that a continuous voltage output, linearly related to the frequency difference is produced.

In use, transmitter/receiver arrangements will preferably be spread across the width of the sheet product. This is possible since it is possible to set up each transmitter/receiver arrangement to transmit and receive a predetermined frequency band. The use of the phase locked loop mechanism in each arrangement enables each of the individual continuous swept frequency waves to be distinguished from one another. Preferably, the piezo-electric devices will contact at least one side of the sheet product.

Respective continuous swept frequency waves may be propagated in the sheet product, (whilst it is on-line) and received by the receiver and further filtered by the phase locked loop. The frequency of the input (or generation) signal is compared with the frequency of the received signal and any difference in the values is due to the delay between transmission and reception. Having knowledge of the distance between the transmitter and receiver, the wave velocity can be calculated and an approximation of strength modulus can be obtained.

Similarly, by offsetting the frequency of the reference wave it is possible to measure both longitudinal and shear modulus using the same equipment. Also, the modulus in the Z-direction can also be obtained by using the method and apparatus of the present invention.

Figure 3:
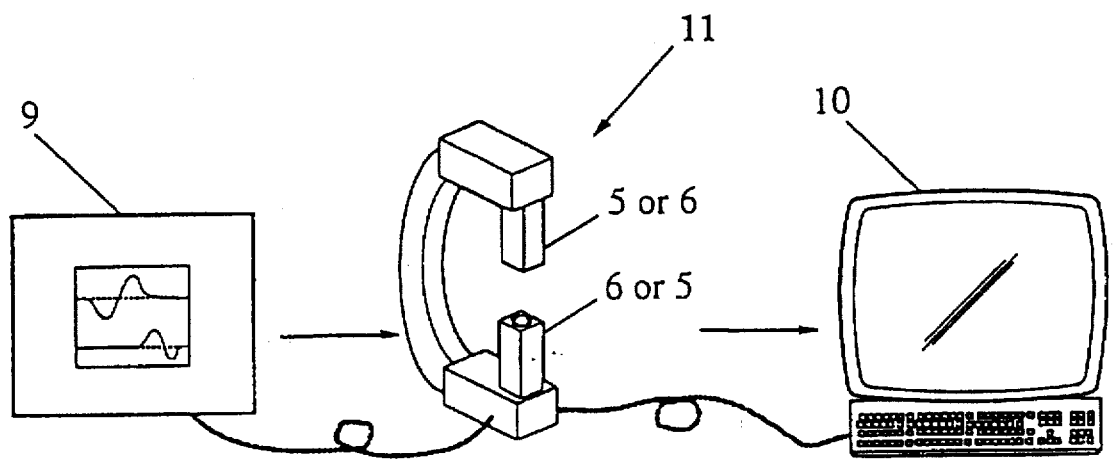
FIG. 3 illustrates an example of a testing rig suitable for measuring Z-direction modulus.

The testing apparatus shown in FIG. 3 consists of a means to generate a signal (9), a sample testing means (10) and a means for analysing the results (10). In most cases a computer is used for analysis of results. The sample testing means (11) consists of a transmitting means (5) and a receiving means (6). The sample (not shown) is placed between the transmitting and receiving means for measurement.

Figure 4:
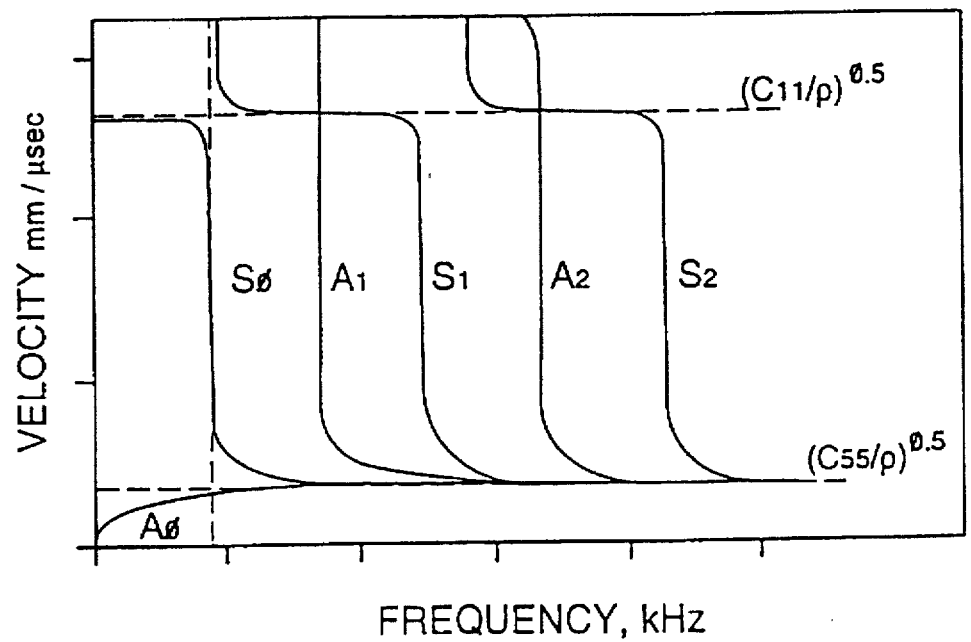
FIG. 4 illustrates a dispersion map of a paper sample.

The characteristics of a paper sample can be represented by a dispersion map. This is preferably represented as a graph with velocity on the vertical axis and frequency on the horizontal axis. An example of a dispersion map generated in the machine direction of a paper sample is shown in FIG. 4. The velocity and frequency shown both refer to ultrasonic waves which are transmitted through the paper sample. Dispersion maps will vary depending on whether the sample is in a longitudinal direction or a shear direction orientation.

Dispersion is the frequency dependence of wave velocity in materials. The frequency of the wave changes the speed at which the wave travels in a material. In the case of paper the frequency dependence of a sound wave travelling through paper is quite marked. This is due to the scattering of fibres and their size relative to the wavelength of the propagated wave.

The dispersion map, generated by the apparatus and method of this invention can be used to provide valuable in-process information about the characteristics of a sample of paper. Furthermore, as the apparatus and method can be used on-line, information about the paper sample can be obtained easily and rapidly.

Prior to the development of the method subject of this invention, dispersion curves have been difficult to generate by time-of-flight pulse techniques because there are a number of modes occurring at the same frequency. These modes interfere with each other and make the measurements difficult to interpret. However, the continuous swept wave method accepts a received signal that falls within a certain propagation delay interval. The dispersion map is built up by sweeping the transmitted frequency but only accepting received frequencies that correspond to a narrow range of wave velocities. A suitable range of transmitted frequencies is from 10 k Hz to 2 MHz.

The paper manufacturing process results in paper symmetry conditions defined by nine elastic properties.

$C_{11}$ is the machine direction elastic stiffness constant
$C_{22}$ is the cross direction elastic stiffness constant
$C_{33}$ is the Z-direction elastic stiffness constant (Z-modulus)
$C_{44}$ is the machine direction -Z-direction shear stiffness
$C_{55}$ is the cross direction -Z-direction shear stiffness
$C_{66}$ is the machine direction-cross direction shear stiffness
$C_{12}$ is an in-pane stiffness
$C_{13}$ is an out-of-plane shear stiffness
$C_{23}$ is an out-of-plane stiffness A dispersion map generated in the machine direction for a sample provides a value for $C_{11}$ which is the elastic stiffness constant for the machine direction. This is represented by the horizontal asymptote of dispersion curves $S_1$ to $S_n$ (see FIG. 3). The velocity measurement obtained from this asymptote is equal to $(C_{11}/\rho)^{0.5}$ ($\rho$ is apparent density).

Furthermore, $C_{55}$, the out-of-plane sheer modulus, can be obtained by measuring the plateau of the dispersion curve $A_0$. This measurement is also taken with the sample in the machine direction and the velocity is equal to $(C_{55}/\rho)^{0.5}$.

Use of this information, in conjunction with the value of $C_{33}$, the out-of-plane modulus allows for calculation of the value of $C_{13}$ (out-of-plane shear stiffness). ($C_{33}$ can be measured independently by methods known in the art such as time-of-flight).

$$\omega_n = \frac{2\pi n}{h} \sqrt{\frac{C_{11}}{\rho} \frac{C_{33}C_{55}}{C_{13}(2C_{55}+C_{13})+C_{11}C_{55}}} \quad (1)$$

where n is the order of the wave mode;

$\omega_n$ is the frequency where the sharp vertical asymptotes occur;

h is the apparent thickness of the paper; and $C_{ij}$ are the various elastic stiffnesses.

(Mann, R. W., Baum, G. A., and Habeger, C. C., "Determination of all nine orthotropic elastic constants for machine made paper." Tappi, February 1980, Vol. 63, No.2, pp 163–166).

The generation of a dispersion map in the cross direction gives valuable information also. The velocity of the horizontal asymptote of the dispersion curves $S_1$ to $S_n$ is equal to $(C_{22}/\rho)^{0.5}$ ($C_{22}$ is the cross direction elastic stiffness constant). Furthermore, the velocity of the plateau of $A_0$ is equal to $(C_{44}/\rho)^{0.5}$ ($C_{44}$ is the machine direction -Z-direction shear stiffness). Using formula (1) above it is therefore possible to substitute $C_{22}$ for $C_{11}$ and $C_{44}$ for $C_{55}$ so as to obtain $C_{23}$ instead of $C_{13}$.

It is also possible to calculate $C_{66}$ (the stiffness defined by the velocity of a shear wave in the plane of the paper sheet) and $C_{12}$ from the information already obtained.

$$C_{66} = 0.387 \sqrt{C_{11}C_{22}} \quad (2)$$

(Mann et al)
and $$C_{12} = \sqrt{\left[2\rho V_{s45}^2 - \tfrac{1}{2}(C_{11}+C_{22}) - C_{66}\right]^2 - \left[\tfrac{(C_{11}-C_{22})}{2}\right]^2} - C_{66} \quad (3)$$

where $V_{S45}$ is the velocity of the in-plane shear wave propagated in a direction 45° to the machine and cross directions (Mann et al). As the in-plane shear velocity has been found to be relatively independent of the direction of propagation, $V_{S45}$ may be adequately replaced with the shear velocity obtained from formula (2) to give:

$$C_{12} = \sqrt{\left[C_{66} - \tfrac{1}{2}(C_{11}+C_{22})\right]^2 - \left[\tfrac{(C_{11}-C_{22})}{2}\right]^2} - C_{66} \quad (4)$$

(Mann et al).

Thus, measurement of the position of the vertical and horizontal asymptotes for the various modes coupled with the out-of-plane stiffness can potentially provide all the system parameters.

Alternatively the dispersion curves generated by a sample can provide information about $C_{33}$, the out-of-plane modulus. The following formula is used:

$$C_{33} = \rho \left(\frac{\omega_n h}{2\pi n}\right)^2 \quad (5)$$

where $\omega_n$ can be measured from the dispersion map; and
h=thickness of the sample.

This formula is based on the assumption that $C_{13}$ (and $C_{23}$) is relatively small which is the case for most paper samples.

The use of this formula (5) in conjunction with the apparatus and method of this invention allows for the determination of the out-of-plane modulus whilst making in-plane measurements.

In general, the thickness of a sample is measured off-line. This is done by any of the known methods.

Alternatively, the thickness of a paper sample can be ascertained by measuring the bending stiffness of the sample. This can be determined from $A_0$ on the dispersion map which is the zeroth assymetric flexural wave. Bending occurs at ¼ the wavelength of the frequency so it is therefore possible to read the appropriate velocity from the vertical axis of the dispersion map.

The velocity is then used in the following equation:

$$v = d/t_d$$

where
v is velocity;
d is sample thickness; and
$t_d$ is the time of flight of the wave through the sample in seconds
to determine the sample thickness.

Furthermore, the continuous wave method can be used to measure the Z-modulus directly. This method relies on reflections between surfaces providing nulls or minimas in magnitude as the frequency is swept. As the wave frequency changes standing waves are set up between the sensors which give minima. These standing waves are related to the dimensions and sound velocity of the materials the wave is propagating through. The frequency at which these minima occur will be altered by increasing the time delay between the sensors. This is done by inserting the sample into the apparatus. A knowledge of the thickness of the sample then allows for the interpretation of the shift in null frequencies to give wave speed through the thickness direction of the sample and therefore an estimate of elastic Z-modulus.

Thus, advantageously, the present invention provides a method wherein the problems of noise, reflections, and impedance mismatch are greatly reduced and data results are obtained in real time. By measuring preferred frequency, this provides a relatively accurate, quantitative method of determining the wave velocity through the sheet product. By comparison, the prior art methods relied upon the comparison of the pulse amplitude or shape transmitted and received, which as indicated previously, was particularly inaccurate, due to the sensitivity of the signal, and time-consuming because of the methods which were necessary to overcome the problems with the system.

We claim:

1. A method of measuring strength characteristics and related properties in a sheet product including the steps of:
    (a) providing a continuous sonic swept frequency wave within the sheet product;
    (b) receiving the continuous sonic swept frequency wave;
    (c) taking measurements in order to ascertain the time the wave takes to reach the receive after transmission and determining the strength characteristics and related properties from said measurements.

2. A method according to claim 1 wherein the swept frequency wave is an ultrasonic swept frequency wave.

3. A method according to claim 1 wherein in order to ascertain the time the wave takes to reach the receiver after transmission, the change in the frequency of the signal transmitted to that received is determined.

4. A method according to claim 2 wherein the ultrasonic swept frequency wave is a linear sweep with constant amplitude.

5. A method according to claim 4 wherein the duration of the linear sweep is equal to the measurement time.

6. A method according to claim 3 wherein a phase locked loop is used to separate and compare desired frequencies.

7. A method according to claim 6 wherein the phase locked loop is a digital phase locked loop.

8. An apparatus for measuring strength characteristics and related properties in a sheet including:
    (a) means to transmit a continuous sonic swept frequency wave within the sheet product;
    (b) means to receive the continuous sonic swept frequency wave; and
    (c) means for taking measurements in order to ascertain the time the wave takes to reach the receiver after transmission so as to determine the strength characteristics and related properties.

9. An apparatus as claimed in claim 8 wherein the means to transmit a continuous sonic swept frequency wave transmits an ultrasonic swept frequency wave.

10. An apparatus according to claim 8 wherein the means for taking measurements includes a means for separating and comparing the desired signals and more preferably the frequencies of the signals.

11. An apparatus according to claim 10 wherein the means for separating and comparing the desired signals includes a phase locked loop.

12. An apparatus according to claim 8 including at least two transmission means.

13. An apparatus according to claim 8 including at least two reception means.

* * * * *

UNITED STATES PATENT AND TRADEMARK OFFICE
CERTIFICATE OF CORRECTION

PATENT NO. : 5,672,828
DATED : September 30, 1997
INVENTOR(S) : Russell J. Allan It is certified that error appears in the above-identified patent and that said Letters Patent is hereby corrected as shown below:

Item [54]

On the title page, and Column 1, line 2, in the title, "UTRASONIC" should read --ULTRASONIC--.

Column 1, line 62, "miniraise" should read --minimize--.

Signed and Sealed this

Seventh Day of April, 1998

Attest:

BRUCE LEHMAN

*Attesting Officer*  Commissioner of Patents and Trademarks